United States Patent
Bohls

[11] Patent Number: 5,383,839
[45] Date of Patent: Jan. 24, 1995

[54] EXTERNAL PLATE VALVES FOR CONTROLLING BLOOD FLOW THROUGH A SHUNT OF A CARDIOPULMONARY BYPASS PUMP

[75] Inventor: Fred O. Bohls, Austin, Tex.
[73] Assignee: Thomas M. Runge, Austin, Tex.
[21] Appl. No.: 103,810
[22] Filed: Aug. 10, 1993
[51] Int. Cl.⁶ ............................................. A61M 1/10
[52] U.S. Cl. .................................................. 600/16
[58] Field of Search ................. 600/16, 17, 18; 623/3

[56] References Cited

U.S. PATENT DOCUMENTS

| | | | |
|---|---|---|---|
| 3,518,033 | 6/1970 | Anderson | 600/16 |
| 4,014,318 | 3/1977 | Dockum et al. | 600/16 |
| 4,553,532 | 11/1985 | Bohls | 600/16 |
| 5,006,104 | 4/1991 | Smith et al. | 623/3 |
| 5,300,015 | 4/1994 | Runge | 600/16 |

Primary Examiner—Angela D. Sykes
Assistant Examiner—Kennedy J. Schaetzle
Attorney, Agent, or Firm—Brady, O'Boyle & Gates

[57] ABSTRACT

External inlet and outlet pinch-type plate valves for controlling the blood flow through a compressible shunt of a cardiopulmonary bypass pump wherein the valves are not fixedly connected to the compression chamber or housing of the pump so that the distance between the inlet and outlet valves can be adjusted to thereby allow adjustment of stroke volume to fit the needs of the patient being treated.

7 Claims, 3 Drawing Sheets

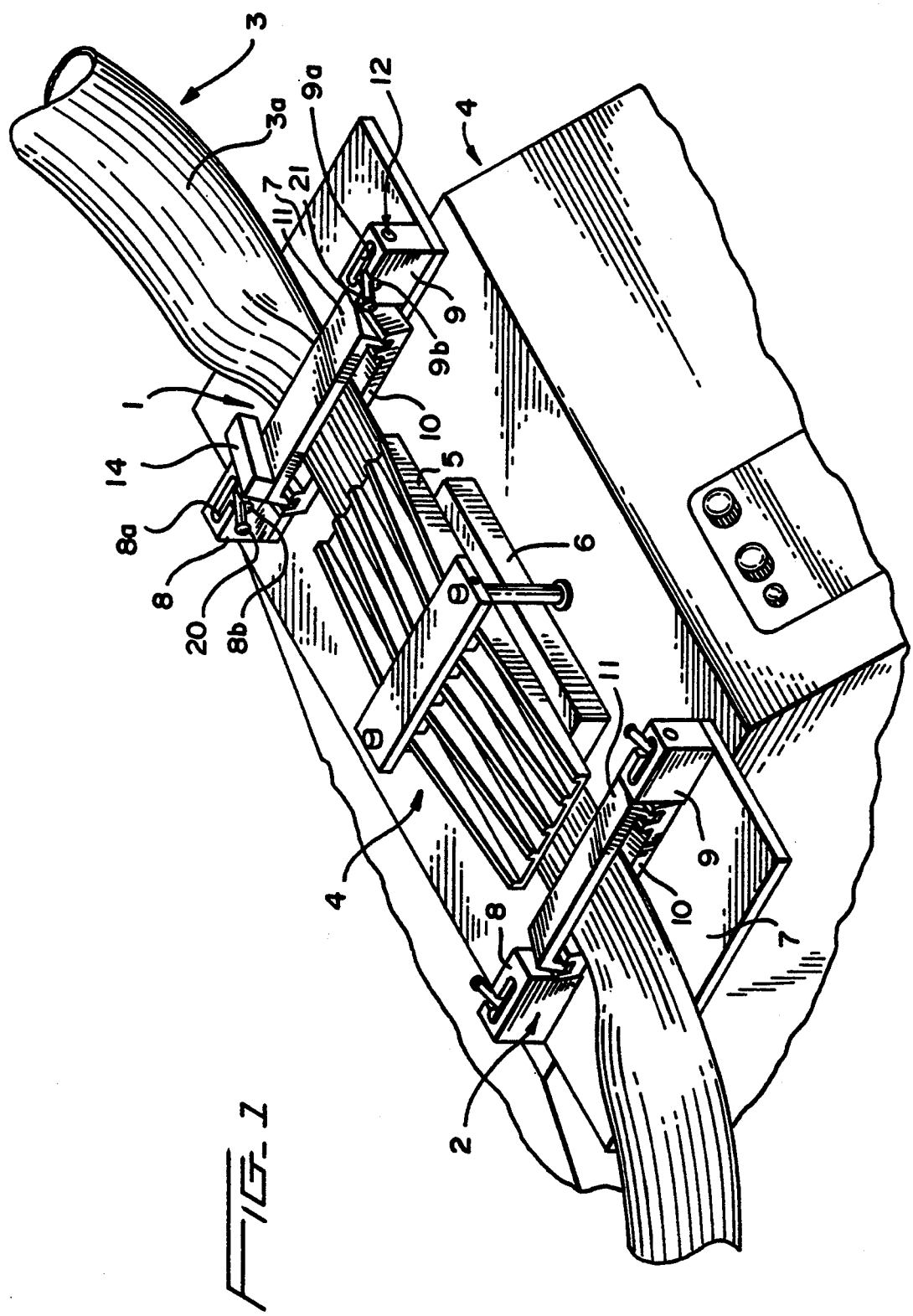

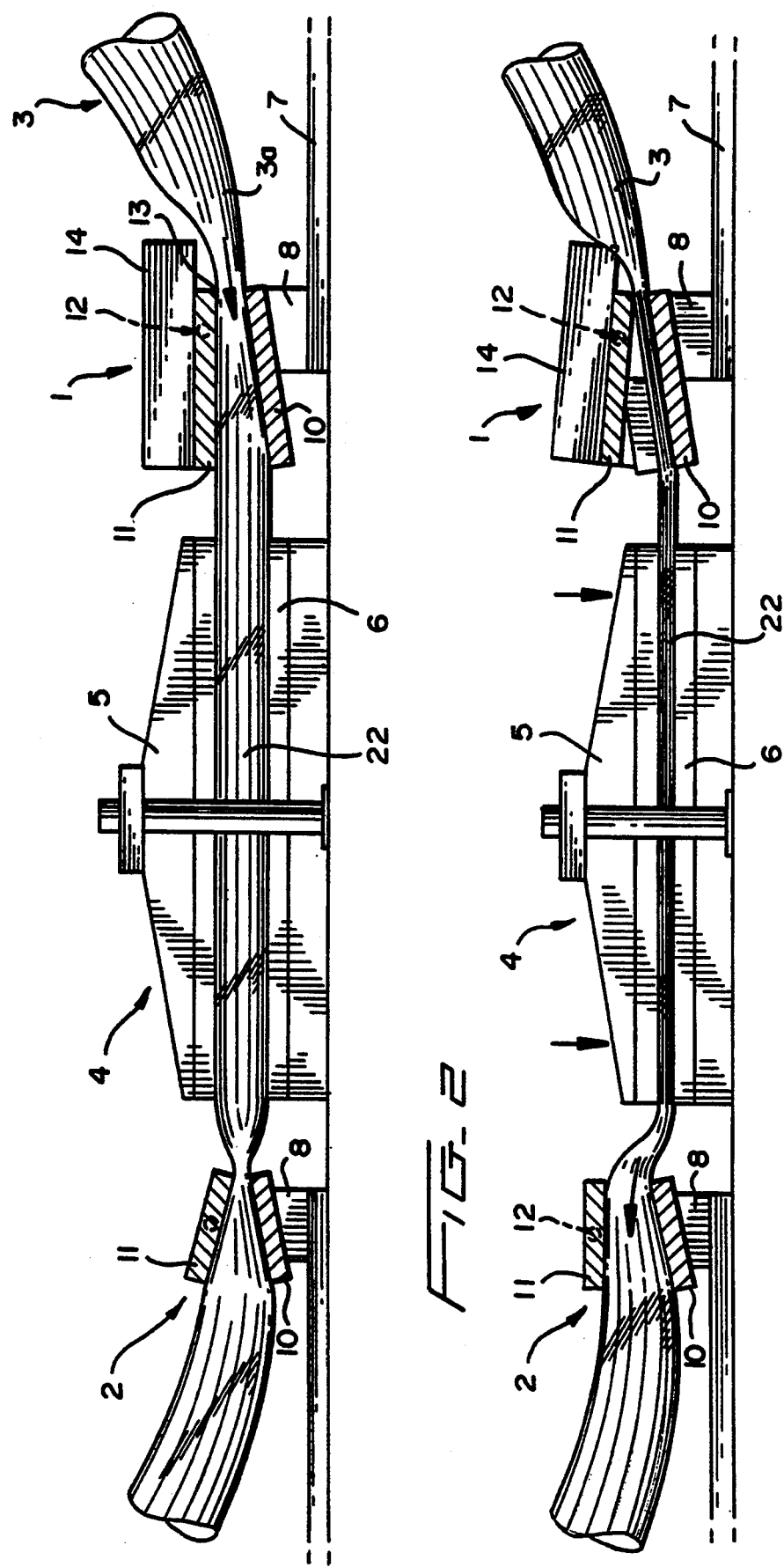

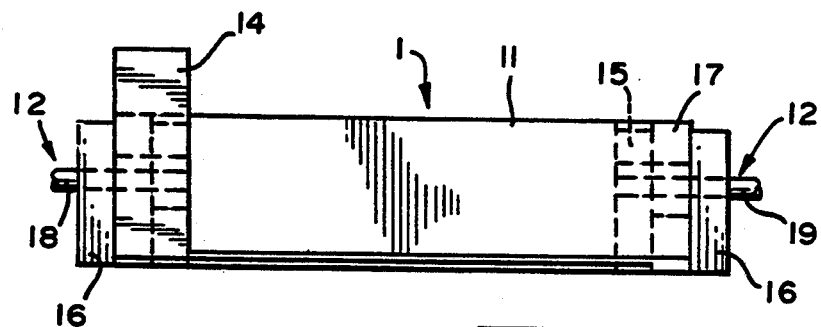
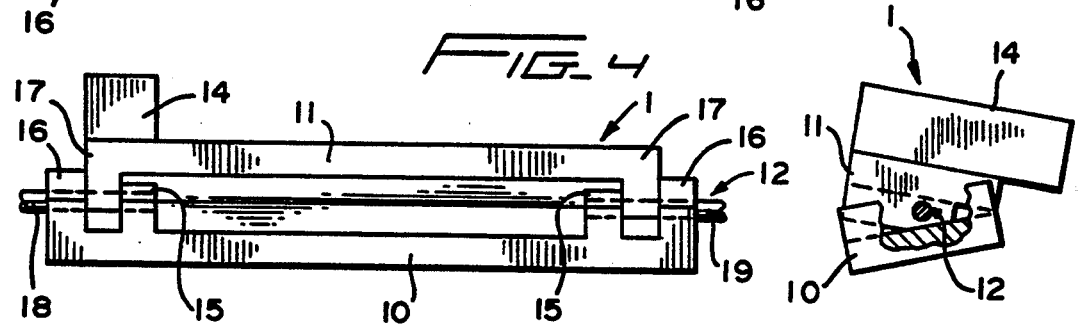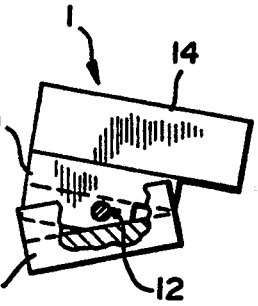
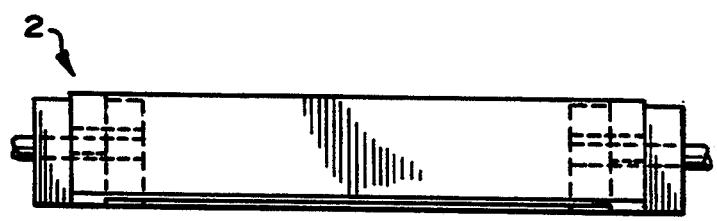
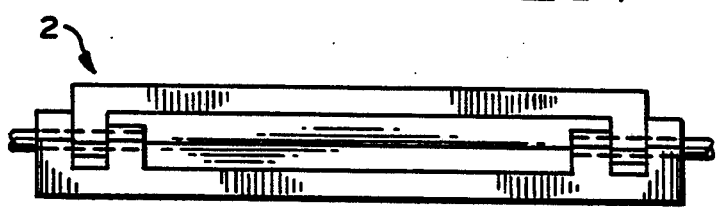

EXTERNAL PLATE VALVES FOR CONTROLLING BLOOD FLOW THROUGH A SHUNT OF A CARDIOPULMONARY BYPASS PUMP

BACKGROUND OF THE INVENTION

An externally valved shunt for a cardiopulmonary bypass pump is disclosed in U.S. Pat. No. 4,553,532, dated Nov. 19, 1985, wherein a suspended roller-like valve element is positioned at the inlet and outlet of a tubing shunt for controlling the flow of blood through the compressible tubing shunt mounted in the compression chamber of a pulsatile flow pump.

While the roller-like valve elements have performed their intended function, the external plate valves of the present invention are an improvement over the roller-like valves disclosed in the above-mentioned patent in that the plate valves of the present invention are not fixedly connected to the compression chamber or housing of the pump so that the distance between the inlet and outlet valves can be adjusted, thereby allowing adjustment of stroke volume to fit the needs of small and large patients, and also to control the degree of hemolysis and lactic acidosis present in the patient.

SUMMARY OF THE INVENTION

Each external plate valve of the present invention comprises, essentially, a base plate, and a pair of spaced blocks mounted on one end of said base plate. An inclined flat plate is positioned in the space between the blocks and is fixed thereto. Another flat plate is positioned above the inclined flat plate and pivoted at each end to a respective block. The pivotal connection of the upper plate to the blocks is provided by a bolt action type assembly, whereby the upper plate can be easily disconnected from the bottom plate to allow a compressible tubing shunt of a cardiopulmonary bypass pump to be inserted between the upper and lower flat plates.

One plate valve is positioned at the inlet side of the cardiopulmonary bypass pump in proximity to the movable compression plate of the pump, and another plate valve is similarly positioned at the outlet side of the pump. By this construction and arrangement, when there is no compression on the shunt by the pump compression plate, the inlet valve is in the open position allowing blood to flow into the shunt and the outlet valve is in the closed position to prevent the flow of blood from the shunt. As the pump compression plate descends to compress the shunt, the inlet valve is pivoted to the closed position and the outlet valve is pivoted to the open position to allow blood to flow from the shunt. As the pump compression plate ascends to the initial position, the outlet valve is pivoted to the closed position and the inlet valve is once again pivoted to the open position.

BRIEF DESCRIPTION OF THE DRAWINGS

FIG. 1 is a perspective view of the external plate valves of the present invention positioned at the inlet and outlet sides of a cardiopulmonary bypass pump;

FIG. 2 is a side elevational view, partly in section, showing the inlet plate valve pivoted to the open position, and the outlet valve in the closed position;

FIG. 3 is a side elevational view, partly in section, showing the inlet valve pivoted to the closed position and the outlet valve pivoted to the open position;

FIG. 4 is a top plan view of the inlet plate valve;

FIG. 5 is a side elevational view of the inlet plate valve;

FIG. 6 is an elevational view of the inlet plate valve, partly in section, showing the valve pivoted to the closed position;

FIG. 7 is a top plan view of the outlet plate valve;

FIG. 8 is a side elevational view of the outlet plate valve; and

FIG. 9 is an end elevational view of the outlet plate valve, partly in section, showing the valve pivoted to the closed position.

BRIEF DESCRIPTION OF THE PREFERRED EMBODIMENT

Referring to the drawings and more particularly to FIG. 1, the external inlet and outlet plate valves 1 and 2, respectively, are constructed and arranged for controlling blood flow through a compressible shunt 3 of a cardiopulmonary bypass pump 4 of the type disclosed in U.S. Pat. No. 4,553,532 dated Nov. 19, 1985 which includes a movable compression plate 5 and a fixed plate 6.

The inlet valve 1 comprises a base plate 7 and a pair of spaced blocks 8 and 9 mounted on one end of the base plate 7. An inclined flat plate 10 is positioned in the space between the blocks 8 and 9 and fixed thereto. Another flat plate 11 is positioned above the inclined flat plate 10 and is pivotally connected at each end to the lower plate 10 and blocks 8 and 9 as at 12. The space between the lower and upper plates 10 and 11 defines a throat 13 at the entrant portion of the inlet valve 1 through which the compressible shunt 3 extends, and a counterweight 14 is mounted on the top surface of the upper plate 11 to urge the upper plate 11 to the closed position as shown in FIG. 3.

The details of the construction of the pivotal connection 12 are illustrated in FIGS. 1 and 5 wherein it will be seen that pairs of upwardly extending spaced arms 15 and 16 are provided on each end of the lower plate 10, and a depending arm 17 is provided on each end of the upper plate 11. The depending arms 17 are positioned in the space between the arms 15 and 16, and a pair of pivot pins 18 and 19 are insertable through aligned apertures provided in the arms 15, 16 and 17. As will be seen in FIG. 1, each pivot pin 18 and 19 is rotatably and slidably mounted in respective blocks 8 and 9, and is provided with a bolt 20, 21 extendable through slots 8a and 9a and notches 8b and 9b in blocks 8 and 9. By this construction and arrangement, a bolt action is provided, whereby the bolts 20, 21 can be slid in the slots 8a and 9a to move the respective pivot pins 18 and 19 into or out of the apertured arms 15 and 16 to thereby connect or disconnect the flat plates 10 and 11 from each other. When the bolts 20 and 21 have been moved to a position to pivotally connect the plates 10 and 11 together, they are then rotated to the position shown in FIG. 1 to be positioned in the notches 8b and 9b.

The details of the construction of the outlet plate valve 2 are identical to those of the inlet plate valve 1, except the outlet valve 2 does not include the counterweight 14; therefore, the same reference numerals are used for similar components.

To assemble the inlet and outlet valves 1 and 2 with the compression shunt 3 and associated cardiopulmonary bypass pump 4, the upper plates 11 of each valve are disconnected from the blocks 8 and 9, and the base plates 7 carrying the lower plates 10 of the inlet and outlet valves 1 and 2 are positioned at a predetermined distance, depending upon the desired stroke volume required for the particular patient, in proximity to the compression plate 5 and fixed plate 6 of the pump 4. The compressible shunt is inserted between the compression and fixed plates of the pump 4 and supported on the lower plates of the inlet and outlet valves 1 and 2. The upper plates 11 of the inlet and outlet valves are then connected to the blocks 8 and 9. The portion of the compression shunt 3 between the inlet and outlet valves 1 and 2 forms a sack 22.

In the operation of the inlet and outlet valves 1 and 2 for controlling blood flow through the shunt 3 of the cardiopulmonary bypass pump 4, the inlet valve 1 is initially open as shown in FIG. 2 to allow blood to flow into the sack 22. The outlet valve 2 is in the closed position wherein the upper plate 11 is pivoted downwardly to pinch the shunt 3. The opening of the inlet valve 1 and closing of the outlet valve 2 occurs because the systemic pressure in the shunt 3 is greater than the pressure in the sack 22. When the pressure plate 5 compresses the sack 22 as shown in FIG. 3, the pressure in the sack 22 is greater than the upstream pressure in the shunt 3 causing the upper plate 11 in the inlet valve 1 to pivot downwardly whereby the shunt is pinched to the closed position between the lower plate 10 and upper plate 11. The counterweight 14 facilitates the pivoting of the upper plate 12 to the closed position. Since the pressure in the sack 22 is greater than the downstream systemic pressure in the shunt 3, the upper plate 11 in the outlet valve 1 is caused to pivot upwardly to the open position to permit an outflow of blood from the compressed sack 22.

When the compression plate 5 returns to the position shown in FIG. 2, the sack 22 fills passively since the upstream reserve pressure is greater than the pressure in the sack, whereby the inlet valve 1 is moved to the open position, and the outlet valve 2 is moved to the closed position because systemic pressure is once again greater than the pressure within the sack.

From the above description, it will be readily appreciated by those skilled in the art that the external plate valves of the present invention are an improvement over other valve arrangements for controlling the flow of blood through a shunt of a cardiopulmonary bypass pump in that by the construction and arrangement of the plate valves, they can be easily assembled to accommodate the shunt 3, and since they are not fixedly connected to the compression chamber or housing of the pump, they can be positioned at a predetermined distance from each other depending upon the desired stroke volume required for a particular patient.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. An external plate valve for controlling blood flow through a shunt of a cardiopulmonary bypass pump comprising, a base plate, a pair of spaced blocks mounted on one end of said base plate, an inclined flat plate positioned in the space between the blocks, said inclined plate being fixedly connected to said blocks, a flat plate positioned above said inclined flat plate, means for pivoting the flat plate to said blocks, and a compressible tubing shunt of a cardiopulmonary bypass pump being positioned between the inclined flat plate and the upper plate, whereby the upper plate is pivotal in one direction toward the inclined flat plate to pinch the shunt to the closed position, and pivotal in the opposite direction to the open position.

2. An external plate valve according to claim 1, wherein the means for pivoting the flat plate to the blocks comprises a pivot pin extending between each block and a respective side of the upper plate, a slot provided in each block, a bolt connected to each pivot pin extending normal to the longitudinal axis thereof, said bolt extending through said slot, whereby each pivot pin is slidably mounted in its respective block and upper plate side, and a notch provided in each block communicating with the respective slot and extending normal thereto, each bolt being receivable into a respective notch to lock the pivot pins in the operative position, whereby a bolt action assembly is provided for pivoting the upper plate to the inclined plate to thereby facilitate the assembly and disassembly of the plate valve for accommodating the compressible tubing shunt.

3. An external plate valve according to claim 1, wherein a counterweight is mounted on the upper flat plate to facilitate the pivotal movement of the upper flat plate to the closed position.

4. A cardiopulmonary bypass pump comprising, a movable compression plate and a fixed plate, an inlet pinch valve mounted on a first base plate positioned externally of the bypass pump, an outlet pinch valve mounted on a second base plate positioned externally of said bypass pump, a compressible shunt for conveying blood through a patient extending through said pinch valves and positioned between the movable compression plate and the fixed plate, the portion of the shunt extending between the inlet and outlet valves providing a sack, each of the base plates and associated inlet and outlet valves being positionable at a predetermined distance from the bypass pump to vary the volume dimension of the sack, to thereby allow for adjustment of stroke volume required for the particular patient.

5. A cardiopulmonary bypass pump according to claim 4, wherein each pinch valve comprises, a pair of spaced blocks mounted on one end of said base plate, an inclined flat plate positioned in the space between the blocks, said inclined plate being fixedly connected to said blocks, a flat plate positioned above said inclined flat plate, means for pivoting the flat plate to said blocks, the compressible shunt being positioned between the inclined flat plate and the upper plate, whereby the upper plate is pivotal in one direction toward the inclined flat plate to pinch the shunt to the closed position, and pivotal in the opposite direction to the open position.

6. A cardiopulmonary bypass pump according to claim 5, wherein the means for pivoting the flat plate to the blocks comprises a pivot pin extending between each block and a respective side of the upper plate, a slot provided in each block, a bolt connected to each pivot pin extending normal to the longitudinal axis thereof, said bolt extending through said slot, whereby each pivot pin is slidably mounted in its respective block and upper plate side, and a notch provided in each block communicating with the respective slot and extending normal thereto, each bolt being receivable into a respective notch to lock the pivot pins in the operative position, whereby a bolt action assembly is provided for pivoting the upper plate to the inclined plate to thereby facilitate the assembly and disassembly of the plate valve for accommodating the compressible tubing shunt.

7. A cardiopulmonary bypass pump according to claim 5, wherein a counterweight is mounted on the upper flat plate of the inlet valve to facilitate the pivotal movement of the upper flat plate to the closed position.

* * * * *